United States Patent [19]

Bridger

[11] 4,259,254

[45] Mar. 31, 1981

[54] METHOD OF PREPARING LUBRICANT ADDITIVES

[75] Inventor: Robert F. Bridger, Hopewell, N.J.

[73] Assignee: Mobil Oil Corporation, New York, N.Y.

[21] Appl. No.: 34,875

[22] Filed: Apr. 30, 1979

[51] Int. Cl.$^3$ .............................................. C07F 11/00
[52] U.S. Cl. ............................. 260/429 R; 252/42.7
[58] Field of Search ................... 260/429 R; 252/42.7

[56] References Cited

U.S. PATENT DOCUMENTS

| | | | |
|---|---|---|---|
| 2,500,195 | 3/1950 | McDermott | 260/429 R X |
| 2,665,291 | 1/1954 | Fischback | 260/429 R X |
| 2,665,292 | 1/1954 | Fischback | 260/429 R X |
| 3,400,140 | 9/1968 | Rowan et al. | 260/429 R |
| 4,098,705 | 7/1978 | Sakurai et al. | 260/429 R |

FOREIGN PATENT DOCUMENTS

| | | | |
|---|---|---|---|
| 789383 | 1/1958 | United Kingdom | 260/429 R |
| 796630 | 6/1958 | United Kingdom | 260/429 R |

OTHER PUBLICATIONS

Chemical Abstracts 34, 82$^3$ (1940).
Chemical Abstracts 61, 6480 (1964).
Chemical Abstracts 19, 2459b (1925).
Chemical Abstracts 81, 44793n (1974).
Chemical Abstracts 65, 16476b (1966).

*Primary Examiner*—Helen M. S. Sneed
*Attorney, Agent, or Firm*—Charles A. Huggett; Michael G. Gilman; Howard M. Flournoy

[57] ABSTRACT

The invention provides a molybdate compound that is useful in lubricants, especially hydrocarbyl lubricating oils, to reduce friction and to decrease fuel consumption in internal combustion engines.

8 Claims, No Drawings

METHOD OF PREPARING LUBRICANT ADDITIVES

BACKGROUND OF THE INVENTION

1. Field of the Invention

This invention is directed to lubricant additives useful as friction modifiers or reducers. It is further directed to a method of reducing fuel consumption in internal combustion engines by adding the above-referred to additives, hydrocarbyl molybdates to the lubricating oil used therein.

2. Discussion of the Prior Art

Efforts to reduce the amount of fuel consumed by automobile engines and the like have revolved around finding lubricants that reduce the overall friction in the engine, thus allowing a reduction in the engine's energy requirements.

Many of the solutions have been strictly mechanical, as for example, setting the engine for a leaner burn or simply building smaller cars and smaller engines. On the other hand, a considerable amount of work has been done with mineral lubricating oils and greases by modifying them with additives to enhance their friction properties. New synthetic lubricants also have been prepared and compounded for use in today's modern engines.

U.S. Pat. No. 3,400,140 discloses the use of phosphomolybdates as extreme pressure additives. The ethyl homologue of the additive compounds embodied herein has been reported in the literature L. Malatesta, *Gazz. Chem. ital.*, 69, 408 (1939), and R. N. Jowitt and P. C. H. Mitchell, *J. Chem. Soc. A*, 1702 (1970). However, it is oil insoluble and we are not aware of any disclosures in the art of any oil soluble homologues. So far as is known the hydrocarbyl molybdates in accordance with this invention are neither taught nor suggested by any prior reference or combination of references, patent or literature.

SUMMARY OF THE INVENTION

Compounds in accordance with the invention have the general formula:

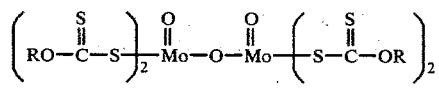

wherein R may be the same or different and is a $C_2$-$C_{30}$ hydrocarbyl group. Accordingly R may be alkyl or cycloalkyl of at least 2 carbon atoms, aryl or alkaryl. R is preferably $C_3$ to $C_{30}$ alkyl and more preferably butyl, pentyl, hexyl, 2-ethylhexyl or dodecyl, etc. When R is aryl, it preferably has from 6 to 14 carbon atoms and when alkaryl from 7 to 18 carbon atoms such as nonylphenyl or dodecylphenyl. Accordingly hydrocarbyl is interpreted herein to mean alkyl, cycloalkyl, aryl or alkaryl as defined above. Usually to ensure oil solubility the total number of carbon atoms in the R groups will not exceed 30. For example, the alkyl group in "alkaryl" is selected such that the total carbon atoms in the aryl and alkyl portions together will not exceed 30.

The invention also provides lubricant compositions containing such compounds and a method for reducing fuel consumption in an internal combustion engine by treating the moving surfaces thereof with the said composition.

Generally speaking the subject additive compounds are prepared by the reaction of an alkali metal, preferably sodium or potassium, or an ammonium alkyldithiocarbonate with a soluble molybdenum (VI) compound in the presence of a suitable reducing agent.

The molybdenum (VI) compound is preferably selected from the following non-exhaustive list sodium molybdate (or hydrates thereof), potassium molybdate, ammonium heptamolybdate tetrahydrate and molybdic oxide ($MoO_3$) solubilized in a base such as sodium or potassium hydroxide and ammonium hydroxide.

Preparation is usually carried out within the following ranges: temperature, from 5° to 60° C.; pressure ambient to 50 psi; reaction time from ½ hr. to 5 hours and in a molar or weight ratio of from 1:1 to 4:1 of alkyldithiocarbonate to molybdenum.

The amount of compound in the lubricant will usefully range from about 0.1% to about 10% by weight of said lubricant, preferably from about 1% to about 5% by weight.

The lubricants contemplated for use with the esters herein disclosed include both mineral and synthetic hydrocarbon oils of lubricating viscosity, mixtures thereof with other synthetic oil and the greases therefrom. The synthetic hydrocarbon oils include long chain alkanes such as cetanes and olefin polymers such as trimers and tetramers of octane and decene. The synthetic oils with which these can be mixed include (1) ester oils such as pentaerythritol esters of monocarboxylic acids having 2 to 20 carbon atoms, (2) polyglycol ethers, (3) polyacetals and (4) siloxane fluids. Especially useful among the synthetic esters are those made from polycarboxylic acids and monohydric alcohols. More preferred are the ester fluids made from pentaerythritol, or mixtures there with di- and tripentaerythritol, and an aliphatic monocarboxylic acid containing from 1 to 20 carbon atoms, or mixtures of such acids.

Having described the invention in general terms, the following are offered to specifically illustrate the development. It is to be understood they are illustrations only and that the invention is not thereby limited except as by the appended claims.

EXAMPLE 1

A solution of ammonium heptamolybdate tetrahydrate (0.1 equiv., 17.6 g) in 100 ml water was added to a cooled (0° to 5° C.) solution of potassium 2-ethylhexyl xanthate (0.2 mol, 48.8 g) in water (100 ml). A stream of sulfur dioxide was introduced into the reaction mixture and excess $SO_2$ was allowed to pass through the stirred solution for one hour, while it gradually warmed to room temperature. The organic phase was taken up in hexane (500 ml), washed twice with 200 ml water, and separated. Solvent removal by rotary evaporation yielded 36.5 g (68.9% yield) of crude -oxo-bis[oxobis(0-2-ethylhexyldithiocarbonato)molybdenum(V)], as a red oil, contaminated with an undetermined quantity of the corresponding dixanthogen. The subject additives are characterized by carbon-13 NMR and, especially, by a charge transfer peak in the visible spectrum. Photoelectronic spectrum, $\lambda_{max}$507 nm. The carbon-13 NMR spectrum of the alkyl group is summarized below. Predicted values were calculated from the rules given by: J. B. Stothers, "Carbon-13 NMR Spectroscopy," Academic Press, New York, 1972, pp. 58, 142.

```
                            CH3      Calcd. δc   Obsvd. δc
                             |         11.7        11.7
                            CH2       24.0        23.7
                             |                       S
                             |                       ||
  CH3—CH2—CH2—CH2—CH——CH2—O—C
  Calcd.
   δc    13.8   23.2   32.6   30.5   40.4   78
  Obsvd.
   δc    14.0   22.9   30.1   28.9   38.9   77
```

Anal. Calcd. for $C_{36}H_{68}O_7Mo_2S_8$: C, 40.74; H, 6.46; Mo, 18.08; S, 24.17. Found: C, 47.67; H, 8.03; Mo, 11.05; S, 23.69.

EXAMPLE 2

The same procedure as Example 1 was used, except that the reaction time was three hours. The product was 34.3 g of red oil, with analysis, visible spectrum and carbon-13 NMR spectrum substantially the same as Example 1.

EVALUATION OF THE PRODUCT

Low Velocity Friction Apparatus (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in$^2$). Both surfaces are submerged in the test lubricant. Friction between the steel surfaces is measured as a function of the sliding speed at a lubricant temperature of 250° F. The friction between the rubbing surfaces is measured using a torquearm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cammoor arrangement.

Procedure

The rubbing surfaces and 12–13 ml. of test lubricant are placed on the LVFA. A 500 psi load is applied, and the sliding speed is maintained at 30 fpm at ambient temperature for a few minutes. A plot of coefficients of friction ($U_k$) over a range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 500 psi, and 30 fpm sliding speed. Freshly polished steel specimens are used for each run. The surface of the steel is parallel ground to 15 to 20 microinches.

The data obtained are shown in Table 2.

| Additive | Conc. % Wt. | % Change in Coeff. of Friction Relative to Base Oil[a][b] | |
|---|---|---|---|
| | | 5 ft/min | 30 ft/min |
| Example 1 | 4 | 63 | 59 |

[a] The base oil is a lubricating oil comprising about 66% by weight of a synthetic hydrocarbon fluid (SHC) and about 20% by weight of an ester fluid. The SHC has a typical viscosity at 210° F. of about 7.0 cSt., and the ester fluid has a typical viscosity at 0° F. of 10.0 cSt. The percentages by weight are percentages by weight of the total lubricating oil composition, including the usual additive package.

[b] The data are percent decrease in friction according to:

$$\frac{(\text{Friction of oil alone}) - (\text{Friction of additive plus oil})}{(\text{Friction of oil alone})} \times 100$$

Thus, the corresponding value for the oil alone would be zero for the form of the data used.

I claim:

1. A process for preparing a compound suitable for use in synthetic hydrocarbon oils of lubricating viscosity of the formula:

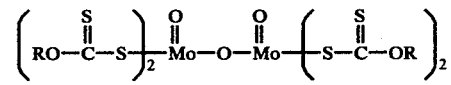

comprising the step of reacting a metal molybdate or an ammonium molybdate with a hydrocarbyl dithiocarbonate acid in a mole ratio of molybdates to dithiocarbonate acid of from about 1:1 to 4:1 at a temperature of from 5° to about 60° C. and a pressure of from ambient to 50 psi for about 0.5 to 5 hours.

2. The process of claim 1 wherein the hydrocarbyl group is an alkyl, a cycloalkyl, an aryl or an alkaryl group.

3. The process of claim 1 wherein the temperature is from about 5° to about 35° C.

4. The process of claim 1 wherein in said composition R is 2-ethylhexyl.

5. The process of claim 1 wherein in said composition R is butyl.

6. The process of claim 1 wherein in said composition R is n-butyl.

7. The process of claim 1 wherein in said composition R is pentyl.

8. The process of claim 1 wherein in said composition R is heptyl.

* * * * *